United States Patent [19]

Totsuka et al.

[11] Patent Number: 5,240,911
[45] Date of Patent: Aug. 31, 1993

[54] METHOD OF REDUCING BLOOD SUGAR LEVELS USING A HYPOGLYCEMIC AGENT

[75] Inventors: Yasuo Totsuka, Kawasaki; Itaru Kojima; Etsuro Ogata, both of Tokyo; Makoto Shiozaki, Kawasaki; Shigeru Shioya, Kawasaki; Hiroshiro Shibai, Kawasaki; Yuzuru Eto, Kawasaki, all of Japan

[73] Assignee: Ajinomoto Co., Inc., Tokyo, Japan

[21] Appl. No.: 410,402

[22] Filed: Sep. 21, 1989

[30] Foreign Application Priority Data

Sep. 22, 1988 [JP] Japan .................... 63-238482

[51] Int. Cl.$^5$ ............................. A61K 37/02
[52] U.S. Cl. ................................. 514/12; 530/350
[58] Field of Search .................. 514/2, 12; 530/350

[56] References Cited

U.S. PATENT DOCUMENTS 4,740,587  4/1988  Ling et al. ................. 530/328

OTHER PUBLICATIONS

Mason et al. "Complementary DNA Sequences of Ovarian Follicular Fluid Inhibin Show Precursor Structure and Homology with TGF-B" *Nature* 318 pp. 659–663 (1985).

*Primary Examiner*—Robert J. Hill, Jr.
*Assistant Examiner*—Shelly Guest Cermak
*Attorney, Agent, or Firm*—Oblon, Spivak, McClelland, Maier & Neustadt

[57] ABSTRACT

Pharmaceutical compositions containing the polypeptides BUF-3, BUF-4 and BUF-5 have hypoglycemic activity. BUF-3 is a homodimer of monomer A shown in FIG. 1. The monomer has a molecular weight of 16±1 kd. BUF-4 is a heterodimer of monomer A and monomer B (FIG. 2). These products can be produced by cell culture of malignant leukemia cells or by recombinant DNA engineering.

4 Claims, 8 Drawing Sheets

```
  1                                          10
Gly Leu Glu Cys Asp Gly Lys Val Asn Ile
 11                                          20
Cys Cys Lys Lys Gln Phe Phe Val Ser Phe
 21                                          30
Lys Asp Ile Gly Trp Asn Asp Trp Ile Ile
 31                                          40
Ala Pro Ser Gly Tyr His Ala Asn Tyr Cys
 41                                          50
Glu Gly Glu Cys Pro Ser His Ile Ala Gly
 51                                          60
Thr Ser Gly Ser Ser Leu Ser Phe His Ser
 61                                          70
Thr Val Ile Asn His Tyr Arg Met Arg Gly
 71                                          80
His Ser Pro Phe Ala Asn Leu Lys Ser Cys
 81                                          90
Cys Val Pro Thr Lys Leu Arg Pro Met Ser
 91                                         100
Met Leu Tyr Tyr Asp Asp Tyr Gln Asn Ile
101                                         110
Ile Lys Lys Asp Ile Gln Asn Met Ile Val
111
Glu Glu Cys Gly Cys Ser
```

*FIG. 1*

```
 1                                              10
Gly Leu Glu Cys Asp Gly Arg Thr Asn Leu
11                                              20
Cys Cys Arg Gln Gln Phe Phe Ile Asp Phe
21                                              30
Arg Leu Ile Gly Trp Asn Asp Trp Ile Ile
31                                              40
Ala Pro Thr Gly Tyr Tyr Gly Asn Tyr Cys
41                                              50
Glu Gly Ser Cys Pro Ala Tyr Leu Ala Gly
51                                              60
Val Pro Gly Ser Ala Ser Ser Phe His Thr
61                                              70
Ala Val VAl Asn Gln Tyr Arg Met Arg Gly
71                                              80
Leu Asn Pro Gly Thr Val Asn Ser Cys Cys
81                                              90
Ile Pro Thr Lys Leu Ser Thr Met Ser Met
91                                              100
Leu Tyr Phe Asp Asp Glu Tyr Asn Ile Val
101                                             110
Lys Arg Asp Val Pro Asn Met Ile Val Glu
111
Glu Cys Gly Cys Ala
```

*FIG. 2*

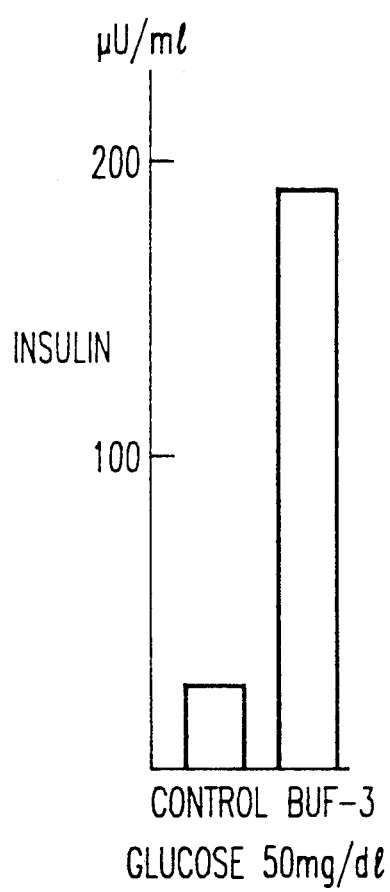
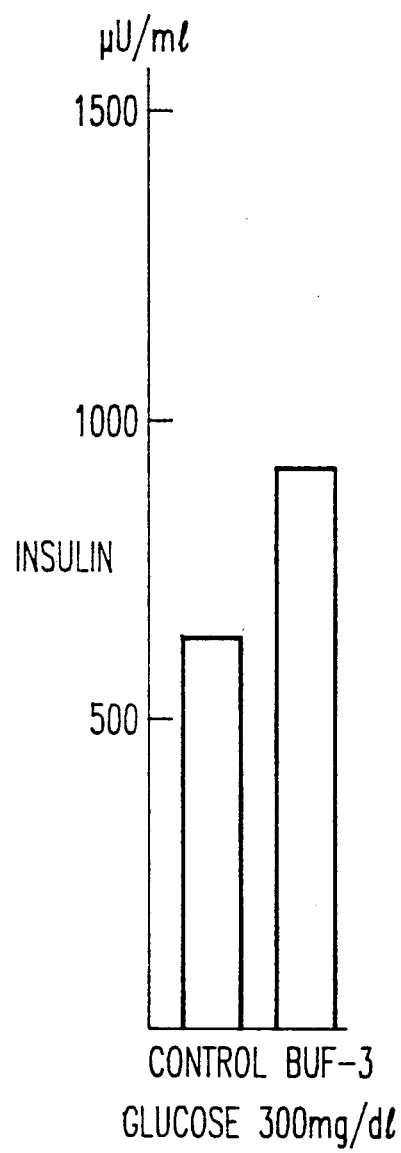
FIG. 8A
FIG. 8B

METHOD OF REDUCING BLOOD SUGAR LEVELS USING A HYPOGLYCEMIC AGENT

BACKGROUND OF THE INVENTION

1. Field of the Invention

The present invention relates to polypeptides which are useful as hypoglycemic agents.

2. Discussion of the Background

Diabetes mellitus is mainly classified into insulin-dependent diabetes mellitus and insulin-independent diabetes mellitus. In the former diabetes mellitus, $\beta$ cells of Langerhans' islet are destroyed by an autoimmune mechanism, whereby secretion of insulin is markedly decreased. For maintenance of life, it is essential to inject insulin every day.

In insulin-independent diabetes mellitus, which is assumed to amount to 95% of all patients with diabetes mellitus in Japan, impairment in the function of pancreatic $\beta$ cells is noted. That is, pancreatic $\beta$ cells of the patient with insulin-independent diabetes mellitus are characterized in that reactivity with glucose is reduced and as a result it is impossible to secret insulin in an amount sufficient to maintain homeostasis of blood sugar. It is quite unknown why such functional impairment occurs on pancreatic $\beta$ cells in insulin-independent diabetes mellitus.

Insulin is the most important hormone for maintaining homeostasis of blood sugar level and is secreted from $\beta$ cells of the endocrine gland in the pancreas. Pancreatic endocrinic tissue includes four kinds of cells: $\alpha$, $\beta$, $\delta$ and PP; which are known to secrete glucagon, insulin, somatostatin, pancreatic polypeptide, respectively. These four kinds of cells gather in large quantities to constitute the pancreatic endocrinic secretion tissue called Langerhans' islets. Langerhans' islets are sporadically present in pancreatic exocrinic secretion tissue and governed by abundant nerves and blood vessels.

There is no doubt that the most important factor for stimulating secretion of insulin from pancreatic $\beta$ cells is glucose. However, it is also believed that regulation with digestive hormones such as GIP etc., or with the autonomic nervous system is also physiologically significant. Furthermore, one cannot ignore that other pancreatic Langerhans' islet hormones, i.e., somatostatin etc., are associated with stimulation of insulin secretion.

As stated above, there are many factors which affect secretion of insulin but the mechanism of these factors on pancreatic $\beta$ cells is unclear in many cases.

In the treatment of diabetes mellitus, oral hypoglycemic agents and insulin therapy are used. Sulfonylureas exhibiting a hypoglycemic activity mainly via accelerated secretion of insulin, and biguanides showing a hypoglycemic activity mainly via the sugar metabolic system have been widely used in oral therapy, but these drugs are not always satisfactory in view of side effects. Insulin therapy is applied to the patient with diabetes mellitus who requires strict control of blood sugar. Since duration of the hypoglycemic activity of insulin is short, multiple insulin injections and continuous subcutaneous insulin injection are clinically adopted in therapy. However, the insulin therapy is painful to the patient and is known to be associated with side effects such as hypoglycemia, allergy, and lipoatrophy at the injected site.

The polypeptide BUF-3 is purified by using the differentiation induction to mouse Freund virus-inducing leukemia cells F5—5. BUF-3 has activity in differentiating and maturing mouse leukemia cells into normal cells (Japanese Patent Application Laid-Open Nos. 234097/1987 and 24070/1987), is used to treat anemia (Japanese Patent Application Laid-Open Nos. 234097/1987 and 24070/1987) and shows activity in secreting folicle stimulating hormone (Nature, 321, 776–779 (1986)).

BUF-3 is also called EDF (Erythroid Differentiation Factor) or FRP (FSH Releasing Protein). The older name BUF-3 is used herein.

It is known that polypeptide BUF-4 has the activity of secreting folicle stimulating hormone (Vale, W., River, J., Vaughan, J., McClintock, R., Corrigan, A., Woo, W., Karr, D. and Spiess, J., Nature, 321, 776–777 (1986)). BUF-4 is also called activin but the name BUF-4 is used herein.

Polypeptide BUF-5 is disclosed in Japanese Patent Application Laid-Open No. 119679/1988.

As described above, BUF-3, BUF-4 and BUF-5 are known and have the activity of releasing folicle stimulating hormone and the like, however hypoglycemic agents containing these polypeptides and a method of treating diabetes mellitus using these polypeptides are unknown.

A need exists therefore for additional hypoglycemic agents with reduced side effects and increased duration of effect.

SUMMARY OF THE INVENTION

Accordingly, one object of the present invention is to provide a novel hypoglycemic agent with minimized side effects and excellent durability.

A further object is to provide a method of treating diabetes mellitus using novel hypoglycemic agents.

These and other objects which will become apparent from the following specification have been achieved by the present hypoglycemic agents BUF-3, BUF-4 and BUF-5 and a method for treating diabetes mellitus using these agents.

BRIEF DESCRIPTION OF THE DRAWINGS

A more complete appreciation of the invention and many of the attentive advantages thereof will be readily obtained as the same becomes better understood by reference to the following detailed description when considered in connection with the accompanying drawings, wherein:

FIG. 1 shows an amino acid sequence of monomer A.

FIG. 2 shows an amino acid sequence of monomer B.

FIGS. 8A and B show the insulin secretion stimulating action of BUF-3 measured by the static incubation method.

DETAILED DESCRIPTION OF THE PREFERRED EMBODIMENTS

Figure 3:
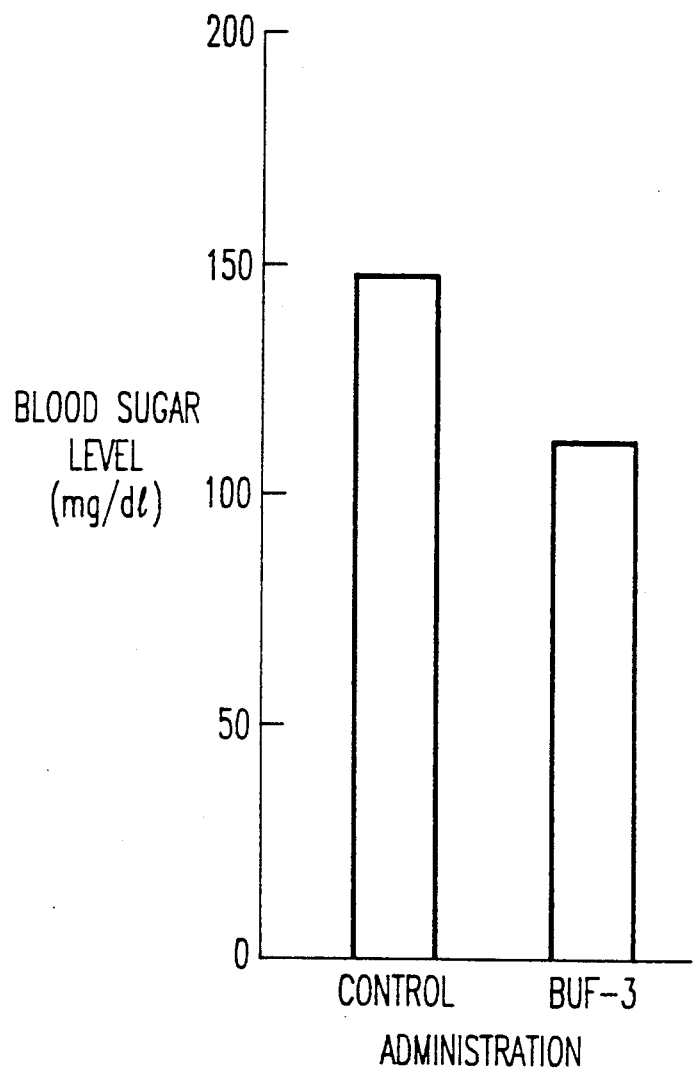
FIG. 3 shows the hypoglycemic activity when BUF-3 was intravenously administered.

It has been discovered that the polypeptide BUF-3 and its analogs BUF-4 and BUF-5 are capable of reducing blood sugar. The hypoglycemic pharmaceutical compositions (agents) of the present invention contain at least one of the polypeptides BUF-3, BUF-4 and BUF-5. Obviously, mixtures of these polypeptides are also possible in the present pharmaceutical compositions.

The hypoglycemic compositions of the present invention which contain at least one of BUF-3, BUF-4, and BUF-5 exhibit excellent and long lasting effects. In multiple insulin injections conventionally used in the clinical field, the duration for hypoglycemic activity is 2 to 4 hours, whereas the hypoglycemic activity in animal tests of BUF-3, BUF-4 or BUF-5 lasts even 24 hours after intravenous injection. For this reason, BUF-3, BUF-4 or BUF-5 can be used as agents for treating diabetes mellitus as substitutes for convention insulin therapy. Furthermore, since the present polypeptides are derived from human protein, the polypeptides have a minimized antigenicity and only a slight tendency to cause allergy so that it is possible to use them over long periods of time.

The hypoglycemic compositions of the present invention exhibit a beneficial effect even on patients with diabetes mellitus who have not improved on insulin therapy.

BUF-3, BUF-4 and BUF-5 are newly discovered, potent insulin secretion stimulating factors. More importantly these polypeptides are present in Langerhans' islets as local regulators for secreting insulin and also play an important physiological role. It is believed that some malfunction participates in the onset of insulin-independent diabetes mellitus. Compositions containing BUF-3, BUF-4 and/or BUF-5 are unique agents for treating insulin-independent diabetes mellitus, in combination with the potent insulin secretion stimulating activity of BUF-3, BUF-4 and/or BUF-5.

The physicochemical properties of the polypeptides BUF-3, BUF-4 and BUF-5 are as follows.

(1) Physicochemical properties of polypeptide BUF-3:
(a) Structure: homodimer of monomer A (see FIG. 1),
(b) Molecular weight: $16\pm1$ kd as monomer (in the presence of 1.0% mercaptoethanol, SDS-electrophoresis); $25\pm1$ kd as homodimer (in the absence of 1.0% mercaptoethanol, SDS-electrophoresis),
(c) Isoelectric point: pI $6.3\pm0.2$ (chromatofocusing) pI 7.3 (isoelectric point electrophoresis),
(d) pH stability: stable in a pH range from 2.0 to 10.0,
(e) Heat stability: stable with heating at 60° C. for 60 minutes,
(f) Stability in organic solvents: stable in lower alcohols and acetonitrile,
(g) Resistance to protease: completely inactivated by treatment with pronase,
(h) Amino acid sequence: the amino acid sequence of monomer A is shown in FIG. 1.

(2) Physiochemical properties of polypeptide BUF-4:
(a) Structure: heterodimer of monomer A and monomer B (see FIG. 2),
(b) Molecular weight: both monomer A and monomer B: $16\pm1$ kd as monomer (in the presence of 1.0% mercaptoethanol, SDS-electrophoresis); $25\pm1$ kd as heterodimer (in the absence of 1.0% mercaptoethanol, SDS-electrophoresis),
(c) Isoelectric point: pI $7.3\pm0.5$ (isoelectric point electrophoresis),
(d) pH stability: stable in a pH range from 2.0 to 10.0,
(e) Heat stability: stable with heating at 65° C. for 60 minutes,
(f) Stability in organic solvents: stable in lower alcohols and acetonitrile,
(g) Resistance to protease: completely inactivated by treatment with pronase,
(h) Amino acid sequence: the amino acid sequences of monomer A and monomer B are shown in FIG. 1 and FIG. 2, respectively.

(1) Physicochemical properties of polypeptide BUF-5:
(a) Structure: homodimer of monomer B (see FIG. 1),
(b) Molecular weight: $16\pm1$ kd as monomer (in the presence of 1.0% mercaptoethanol, SDS-electrophoresis); $25\pm1$ kd as homodimer (in the absence of 1.0% mercaptoethanol, SDS-electrophoresis),
(c) Isoelectric point: pI $7.3\pm0.5$ (isoelectric point electrophoresis),
(d) pH stability: stable in a pH range from 2.0 to 10.0,
(e) Heat stability: stable with heating at 65° C. for 60 minutes,
(f) Stability in organic solvents: stable in lower alcohols and acetonitrile,
(g) Resistance to protease: completely inactivated by treatment with pronase,
(h) Amino acid sequence: the amino acid sequence of monomer B is shown in FIG. 2.

The present invention also includes closely related derivatives of BUF-3, BUF-4 and BUF-5 which also have hypoglycemic activity. As used herein, "polypeptides substantially similar to BUF-3, BUF-4 and BUF-5" means polypeptides having substantially the same amino acid sequence as BUF-3, BUF-4 and BUF-5, but in which one or more of the amino acids in the sequence shown in FIG. 1 or FIG. 2 are replaced with other amino acids, and are considered to be within the scope of the present invention so long as these polypeptides exhibit hypoglycemic activity. For example, polypeptides having one or more additional amino acids added to the N-terminus or C-terminus of the polypeptide show hypoglycemic activity and are within the scope of this invention. The present invention also encompasses structures wherein one or more amino acids are deleted from the N-terminus or C-terminus but the peptide continues to show hypoglycemic activity. Preferred polypeptides are those in which the amino acid sequence of BUF-3, BUF-4 and BUF-5 is at least 60%, preferably 80% and most preferably 90% percent identical to the amino acid sequences shown in FIG. 1 or FIG. 2.

BUF-3, BUF-4 and BUF-5 and their related derivatives possess excellent, long-acting hypoglycemic activity in animal experiments and do not show toxicity in mouse and human cell culture tests. Therefore, BUF3, BUF-4 and BUF-5 are considered to be safe and effective for prophylaxis and treatment of diabetes mellitus.

The hypoglycemic agents of the present invention contain as the effective ingredient at least one of the polypeptides BUF-3, BUF-4 and BUF-5. Thus, the hypoglycemic agent may contain the effective ingredients singly or may contain them as an admixture. In addition, the hypoglycemic agent of the present invention can also be used for purposes of diagnosis of the function of pancreas, etc.

The present hypoglycemic agent is preferably administered parenterally (intravenous, subcutaneous, intramascular, percutaneous, or transmucous).

As for the dosage of the effective ingredient described above, when any substance of BUF-3, BUF-4 and BUF-5 is used singly, a daily dose is generally approximately 0.01 mg to 100 mg for an adult and is administered as a single dose or by dividing into several smaller doses. Further when two or more of BUF-3, BUF-4 and BUF-5 are administered in combination, that is, (a) BUF-3 and BUF-4, (b) BUF-3 and BUF-5, (c) BUF-4 and BUF-5 and (d) BUF-3, BUF-4 and BUF-5, a daily dose is generally also approximately 0.01 mg to 100 mg for an adult and is administered as a single dose or by dividing into several smaller does, since the pharmacological effect of each peptide is almost identical. Of course the dose may vary depending upon blood sugar level, conditions and body weight of the patient and other factors known to one skilled in the art. Hence, it is unnecessary to strictly follow the dose described above and the dose may be determined according to the individual patient's situation.

Medical preparations containing BUF-3, BUF-4 and/or BUF-5 as the effective ingredient can be prepared in a conventional manner and are preferably prepared for injection. Other preparatory forms include capsules, tablets and other well known formulations. When injections are prepared, the main component(s), BUF-3 and/or BUF-4 and/or BUF-5 may be added with, if necessary, a pH controlling agent, a buffer, a stabilizer, a preservative, etc. and prepared into intravenous, subcutaneous or intramascular injections. Further where oral preparations are prepared, the main component(s), BUF-3 and/or BUF-4 and/or BUF-5 may be added with a carrier and, if necessary, further a binder, a disintegrator, a coloring agent, etc. and prepared into tablets, capsules, etc.

BUF-3 can be produced from cell cultures of malignant leukemia cells or by recombinant DNA engineering. Regarding the cell culture, human malignant monocytes capable of producing BUF-3 are exemplified by human leukemia cells or human myeloid cells which are artificially rendered malignant. Specific examples include human chronic myeloid leukemia cells (U-937 ATCC CRL 1593, Int. J. Cancer, 17, 565 (1976), K562, Blood, 45, 321 (1975)), and acute monocytic leukemia cells (THP-1, Int. J. Cancer, 26, 171–176 (1980)). Of course human leukemia cells other than those described above may be used so long as BUF-3 is produced.

A specific differentiation inducer is a substance that can differentiate and induce the malignant monocyte into normal macrophage and normal monocytes of granulocytes when the malignant monocyte is treated by this substance. At the same time, malignant monocytes can produce BUF-3 in the presence of specific substances. Examples of the specific differentiation inducer include actinomycin D, mitomycin C, concanavalin A and phorbol ester (TPA), etc.

To produce BUF-3 of the present invention, malignant monocytes are cultured in the presence of at least one of the aforesaid specific differentiation inducers, whereby BUF-3 is extracellularly produced in the culture solution.

The media used for culturing malignant monocytes are ordinary media used for culturing animal cells. A preferred example is Roswell Park Memorial Institute 1640 medium (RPMI-1640).

Culture of malignant monocytes is carried out generally at a cell density of 1 to $5 \times 10^6$/ml at 35° C. to 38° C., with a carbon dioxide gas flow of 4% to 6% while gently agitating. The specific differentiation inducer may be added at an initial state of the culture or during the course of the culture. The amount added may vary depending upon the kind of differentiation inducer and is generally 0.1 to 10 $\mu$g/ml in the case of actinomycin D, mitomycin C, etc. and 1 to 500 $\mu$g/ml in the case of TPA. When cultured for 1 to 5 days, BUF-3 accumulates in the culture solution.

In addition to hypoglycemic activity, BUF-3 has a differentiation induction activity on Firent virus-inducing leukemia cells F5-5 (Bibl. Haemst., 43, 37 (1976)). Using this activity, qualitative and quantitative assays for BUF-3 can be performed. Assays using F5-5 can be made in accordance with the method described in Proc. Natl. Acad. Sci., 71, 98 (1975). Activity is expressed in terms of an activity per 1.0 ml of stock solution using a reciprocal number of dilution of the stock solution of a sample when differentiation of F5-5 cells is clearly confirmed. When BUF-3 is produced by the method of the present invention, the culture solution indicates an activity of 4 to 1000 units/ml. Thus, the desired BUF-3 is produced. Additional details of this method are described in Japanese Patent Application Laid-Open Nos. 234097/1987 and 240700/1987.

Alternatively, BUF-3 can be produced by recombinant DNA engineering. That is, culturing eucaryotic cells (specifically IFO-50146, etc.) transformed by a plasmid containing a gene encoding BUF-3, i.e., monomer A, and producing BUF-3 in the culture solution (Japanese Patent Application No. 210810/1987; Masahiro Murata, Kazuya Onomichi, Yuzuru Eto, Hiroshiro Shibai and Masami Muramatsu, Biochemical and Biophysical Research Communications, 151 (1), 230–235 (1988)).

Production of BUF-4 and BUF-5 is known and is carried out in a manner similar to the production of BUF-3 by recombinant DNA engineering.

To produce BUF-4, eucaryotic cells transformed by a plasmid containing a gene encoding BUF-4, i.e., monomer A and monomer B, may be cultured in a medium and BUF-4 is produced in the culture solution (Japanese Patent Application Laid-Open No. 119679/1988).

To produce BUF-5, eucaryotic cells transformed by a plasmid containing a gene encoding BUF-5, i.e., monomer B, may be cultured in a medium and BUF-5 is produced in the culture solution (Japanese Patent Application Laid-Open No. 119679/1988).

The produced BUF-3, BUF-4 or BUF-5 can be purified in a manner similar to ordinary purification of polypeptides. Crude polypeptide standards can be obtained, for example, by concentrating the culture solution, salting-out the polypeptide from the concentrate and then performing ion exchange chromatography using an anionic exchanger. By using hydrophobic chromatography or chromatofocusing of the crude standard most protein impurities can be removed. By using both chromatographies in combination the purification can be increased.

The purified standard product can be purified further by performing reversed phase high performance liquid chromatography (HPLC) or high efficiency gel filtration by using the FPLC (manufactured by Pharmacia, Fast Protein Polynucleotide Liquid Chromatography)

system equipped with Super Rose or Mono Q HR5/5 columns or ion exchange chromatography.

In addition to the conventional purification of polypeptides as described above, BUF-3, BUF-4 and BUF-5 may also be purified using organic solvents containing organic acids in a definite concentration as taught in Japanese Patent Application No. 131268/1988.

Other features of the invention will become apparent in the course of the following descriptions of exemplary embodiments which are given for illustration of the invention and are not intended to be limiting thereof.

EXAMPLES

Example 1

BDF$_1$ mice (male, age of 10 weeks, Japan Charles River Co., Inc.) were used as test animals, one group being 6 mice. BUF-3 (freeze dried product added with a 6-fold amount of serum albumin collected from pure line mouse as a carrier) having a specific activity of about $2 \times 10^6$ U/mg was dissolved in physiological saline. The solution was filtered and sterilized to prepare a 100 µg/ml injection. The injection was intravenously administered to the BUF-3-administered group in a dose of 0.1 ml (10 µg of BUF-3) once a day for 5 consecutive days. To the control group, a solution of serum albumin alone collected from pure line mouse in physiological saline, which had been filtered and sterilized, was intravenously administered in a dose of 0.1 ml once a day for 5 days. The animals both in the BUF-3-administered group and in the control group were fasted after the evening on day 5. In the morning on day 6, blood was collected from the heart of the mice in both groups under ethereal anesthesia and the blood sugar levels in whole blood were determined in a conventional manner. Several serum components other than blood sugar level were also simultaneously determined in a conventional manner. The measured blood sugar levels are shown in FIG. 3. The BUF-3-administered group showed average blood sugar levels of 115 mg/dl, which was lower than the 148 mg/dl average of the control group indicating an obviously significant difference.

The measured results of serum components other than blood sugar level are shown in Table 1. With respect to the five serum components examined, no significant difference was noted between the BUF-3administered group and the control group.

TABLE 1

| | Serum Component | | | | |
|---|---|---|---|---|---|
| | GOP (IU/l) | GPT IU/l) | Creatinine (IU/l) | Urinary Nitrogen (mg/dl) | Bilirubin (mg/dl) |
| BUF-3-administered group | 78 ± 19 | 15 ± 3 | 0.5 ± 0.1 | 31.8 ± 3.4 | 0.25 ± 0.04 |
| Control group | 82 ± 12 | 15 ± 3 | 0.5 ± 0.1 | 30.5 ± 1.3 | 0.23 ± 0.02 |

Also with respect of BUF-4 and BUF-5, the same results as BUF-3 may be obtained.

EXAMPLE 2

BDF$_1$ mice (male, age of 10 weeks, Japan Charles River Co., Inc.) were used as test animals, one group being 6 mice. Using the same BUF-3 as used in Example 1, 400 µg/ml of a solution for administration was prepared in a manner similar to Example 1. A miniature-sized osmosis pump (manufactured by ALZA Inc. in USA, Model 2001) was filled with the solution. After mice administered with BUF-3 were laparotomized under anesthesia with pentobarbital, the miniature-sized osmosis pump described above was transferred into the abdominal cavity and the cavity was immediately sutured.

Figure 4:
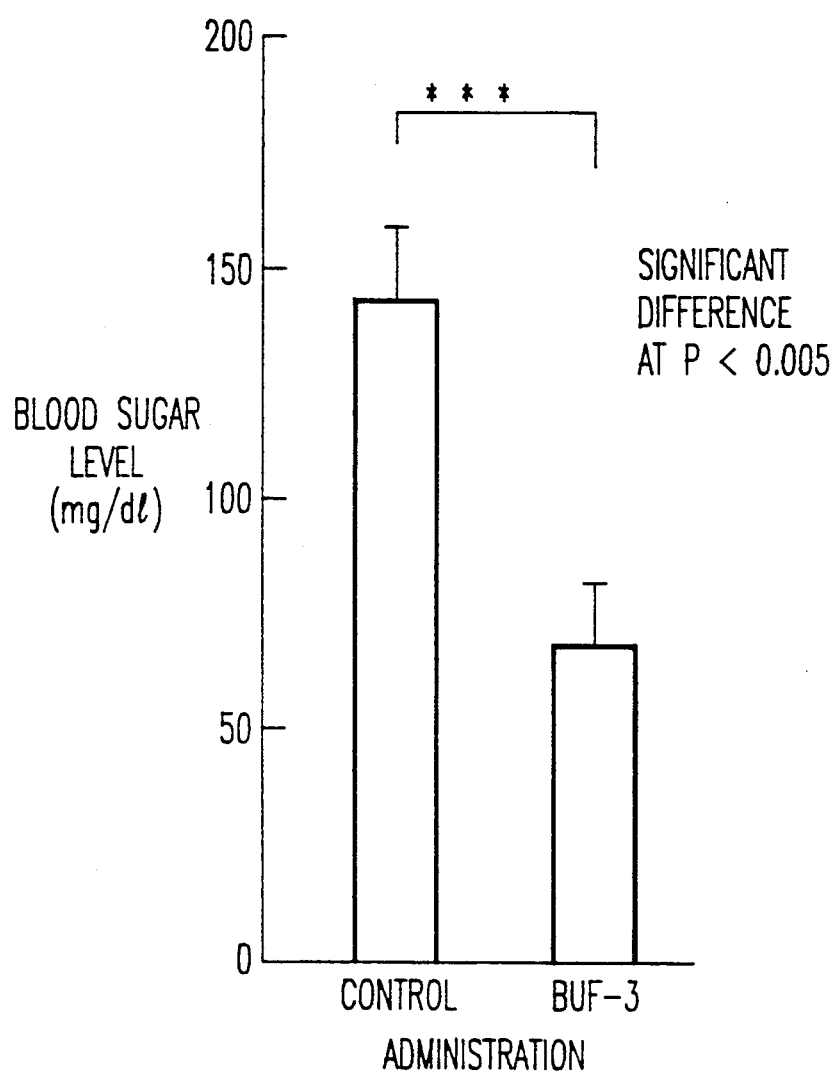
FIG. 4 shows the hypoglycemic activity when BUF-3 was intraperitoneally administered.

For the control group, a miniature-sized osmosis pump filled up with a solution of serum albumin alone, collected from pure line mouse in physiological saline, was transferred to the abdominal cavity in a similar manner. The miniature-sized osmosis pump is a device for releasing the contained solution at a defined rate over 7 days or longer. Model 2001 used in this run has a release rate of 1 µl/hour and BUF-3 is thus intraperitoneally administered continuously at a rate of 400 ng/hour. The mice were fasted after the evening on day 5. In the morning on day 6, blood was collected from the heart of the mice under ethereal anesthesia and blood sugar levels of whole blood were determined in a conventional manner. The measurement results of blood sugar level are shown in FIG. 4. The BUF-3-administered group showed average blood sugar levels of 67 mg/dl, which was significantly lower than the 144 mg/dl average of the control group indicating a much more remarkable reduction in blood sugar level than in the case of intravenously administering BUF-3.

EXAMPLE 3

Langerhans' islets were isolated from rat pancreas as follows. The head of a Wistar strain male rat weighing about 200 g was cut. After blood was withdrawn, the rat was subjected to laparotomy.

The common bile duct was ligated at the duodenal aperture and cannulation was performed from the liver side to swell the pancreas with HANKS-HEPES buffer, whereby the pancreas was taken out.

Fat, lymph nodes, pancreatic duct, etc. were removed from the pancreas on a Petri dish charged with buffer. The pancreas was then chopped into a uniform size of about 0.5 mm with inward scissors in a small beaker. By several rinsing operations, fat tissues, etc. were removed.

Collagenase (manufactured by WAKO, for cell suspension) was added to the chopped pieces in a ratio of 2000 U/ml (25 mg of collagenase/2.5ml KRB buffer (37° C., pH 7.4) per 1 pancreas) followed by vigorous agitation at 37° C. for 6 minutes in an incubator. After digestion with collagenase, the digestion product was diluted with HANKS-HEPES buffer (pH 7.4 at room temperature) and the dilution was precipitated and settled. Sixty seconds later, 25 ml of the supernatant was removed. The operation was repeated 8 times in total. After the last removal of the supernatant, the precipitates were taken up in a tube and centrifuged at 1000 rpm for 10 minutes.

After removing the supernatant by decantation, 27% Ficoll was added to the pellets. The mixture was applied to make it homogeneous. Then, 23%, 20.5% and 11% of Ficoll were laid thereon in sequence so as not to cause distortion of the layers. The system was then centrifuged at 2000 rpm for 15 minutes.

The suspension between 20.5% and 11% was taken out through a pasteur pipette and Langerhans' islets alone were immediately picked up with a micropipette under a stereoscopic microscope. The collected Langerhans' islets were washed with Krebs-Ringer bicarbonate buffer (KRB buffer) in a centrifuging tube of 50 ml to completely remove Ficoll (3 times in total).

The Krebs-Ringer bicarbonate buffer is composed of 115 mM of NaCl, 5 mM of KCl, 1 mM of $Na_2HPO_4$, 1 mM of $MgSO_4$, 2.2 mM of $CaCl_2$, 24 mM of $NaHCO_3$ 20 mM of HEPES and 0.17% of BSA.

After rinsing, 30 pieces each of the islets having the same shape and size were again picked up for the perfusion assay.

For static incubation, one piece each was again picked up into a tube charged with 0.5 ml of medium (50 mg/dl in glucose concentration).

In this case, Langerhans' islets were picked up so as to put the islets having the same shape and size in each tube.

The medium (HANKS-HEPES) used had a composition of: 136.9 mM of NaCl, 5.36 mM of KCl, 0.338 mM of $Na_2HPO_4$. $12H_2O$, 0.441 mM of $KH_2PO_4$, 0.811 mM of $MgSO_4$. $7H_2O$, 1.258 mM of $CaCl_2$. $2H_2$, 3.57 mM of $NaHCO_3$ and 20 mM of HEPES.

EXAMPLE 4

The following method was used as the perfusion assay with KRB buffer used as a basic medium.

The basic medium was previously filtered through a filter (pore size, 0.45 μm) twice, then saturated with a gaseous mixture of 5% of $CO_2$ and 95% of $O_2$ and kept at 37° C. in an incubator.

Next, a medium obtained by incorporating 50 mg/dl of glucose into the basic medium described above and a medium obtained by incorporating 300 mg/dl of glucose into the basic medium were separately passed through independent tubes. The flow rate was adjusted to 0.5 ml/min.

A filter (millipore filter manufactured by Japan Millipore Industry Co., Ltd., pore size of 10 μm) was set in a chamber. After 30 Langerhans' islets obtained in Example 3 were injected through the upper portion of the chamber using a syringe (needle was unnecessary), the chamber was connected with a circuit. In order to keep the Langerhans' islets stable, a medium containing 50 mg/dl of glucose was kept flowing for 20 minutes. Five minutes after completion of the rinsing, sampling was made every one minute. BUF-3 was added to the medium containing 50 mg/dl of glucose in a concentration of $10^{-8}M$ or $10^{-9}$ M and perfusion was conducted for 20 minutes (BUF-3, $10^{-8}M$) or for 40 minutes (BUF-3, $10^{-9}M$), during which sampling was made every 5 minutes or every 1 minute.

The medium containing 300 mg/dl of glucose was perfused 20 minutes or 40 minutes more. BUF-3 was added to the BUF-3+side. Sampling was performed for 10 minutes every 1 minute and then every 5 minutes for a time period of 30 to 200 minutes.

Figure 5:
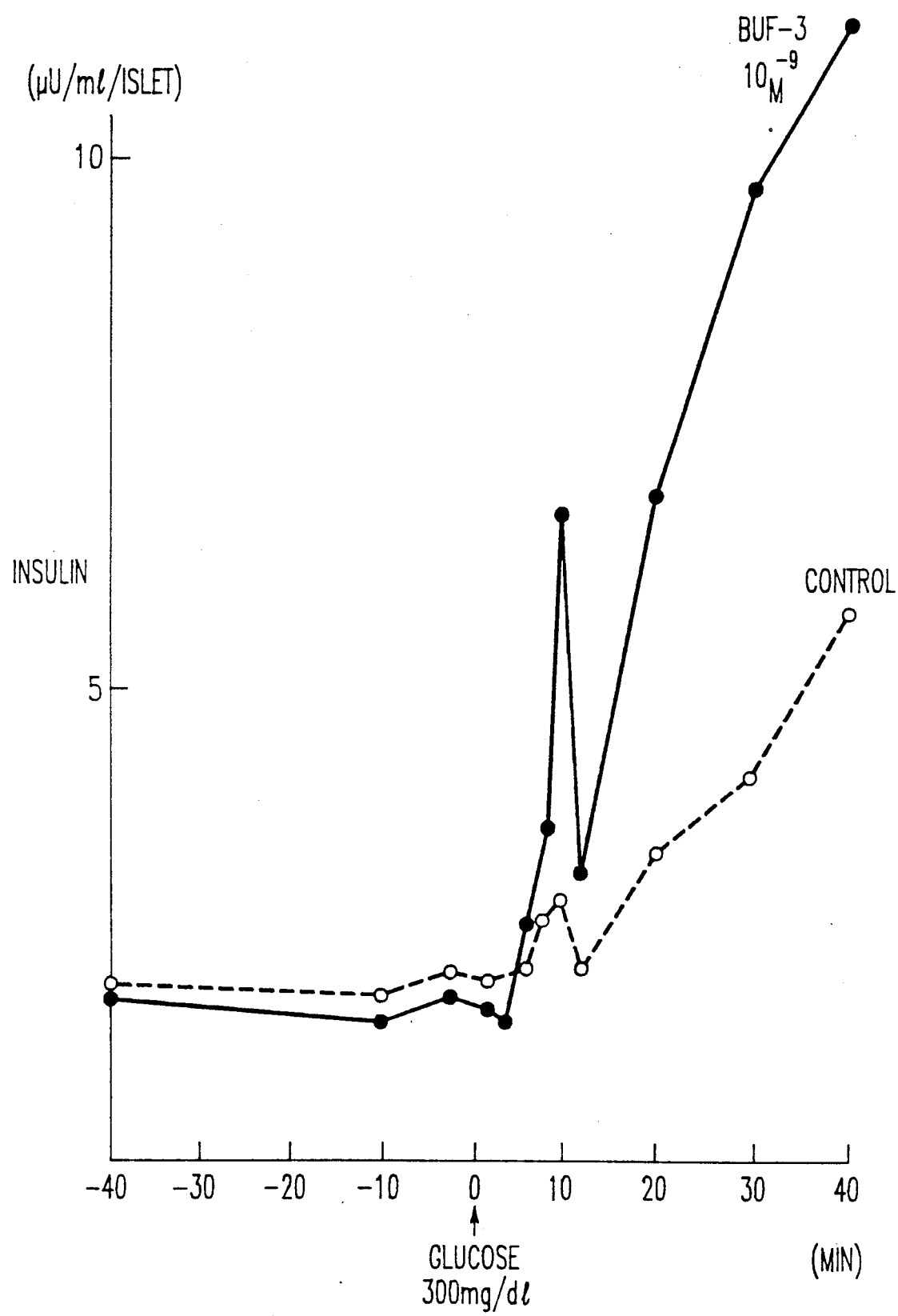
FIG. 5 shows the insulin secretion stimulating action of BUF-3 determined by the perfusion method.
Figure 6:
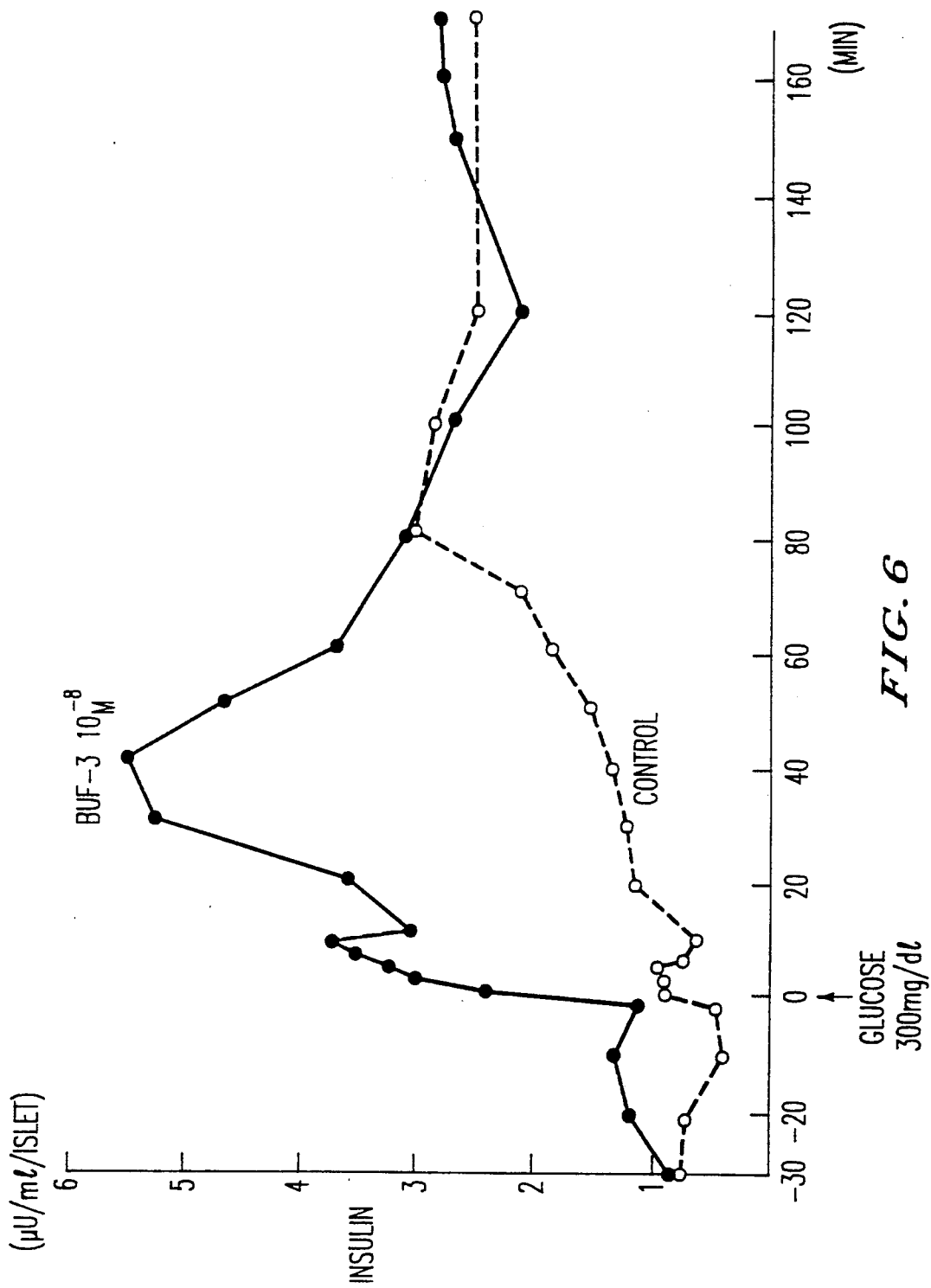
FIG. 6 shows the insulin secretion stimulating action of BUF-3 measured by the perfusion method over long periods of time.

Each concentration of insulin in the media collected by sampling was determined using a $^{125}I$ insulin RIA kit (Daiichi Radioisotope Co., Ltd.). The results obtained with BUF-3 concentrations of $10^{-9}M$ and $10^{-8}M$ are shown in FIGS. 5 and 6, respectively. In both cases, increased secretion of insulin was observed.

EXAMPLE 5

The concentration dependency of BUF-3 was examined by static incubation using the same medium as in Example 4. 1 ml of a medium containing 50 mg/dl of glucose was charged in a test tube and one piece of Langerhans' islets obtained in Example 3 were added to the medium. Then, 10 μl of BUF-3 were added in various concentrations, a gaseous mixture containing 5% of $CO_2$ was charged and the test tube was sealed with a rubber stopper. Two hours later 200 μl of the supernatant was subjected to sampling and the concentration of insulin was determined with $^{125}I$. The results are shown in FIG. 7.

Figure 7:
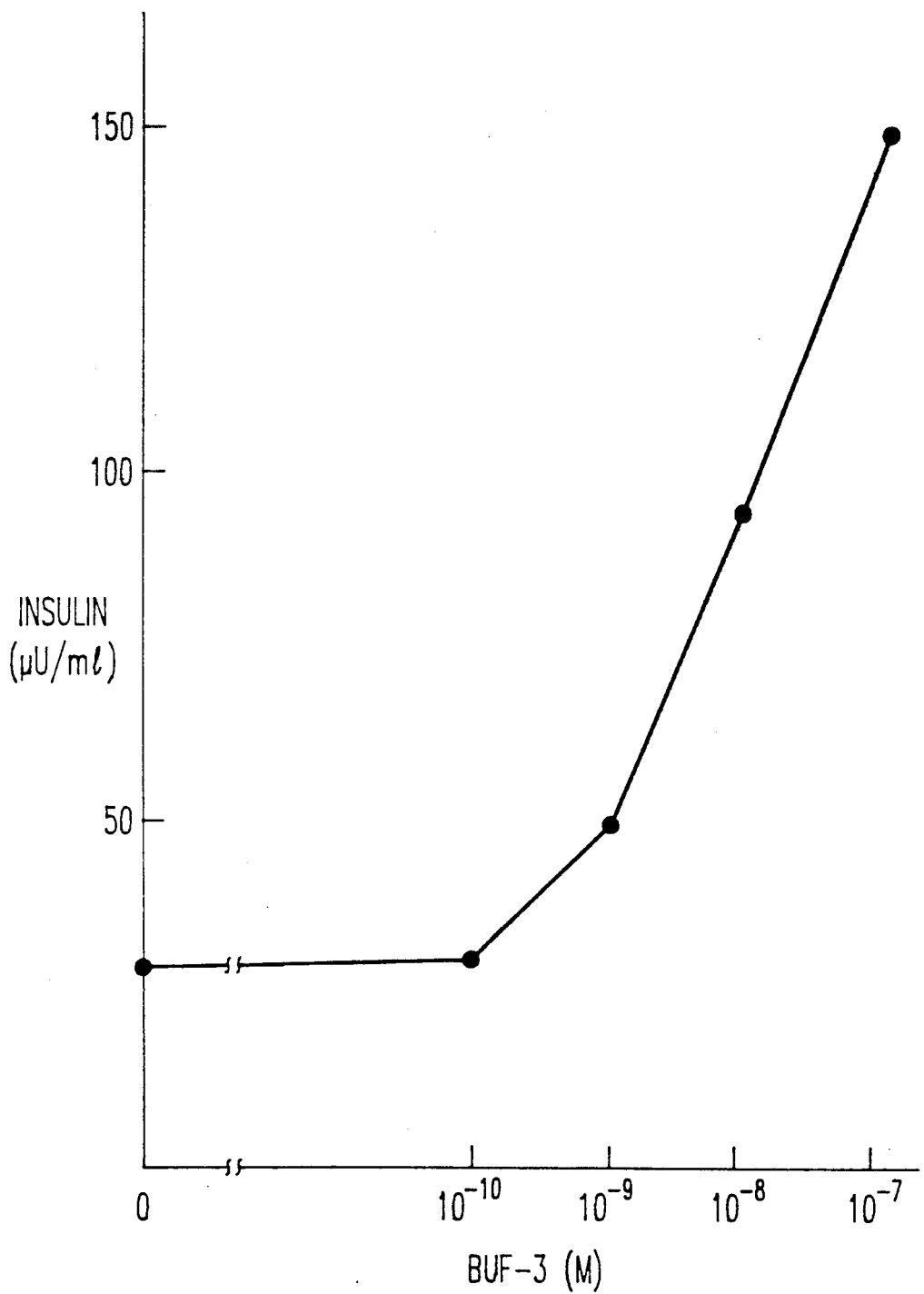
FIG. 7 shows the concentration dependency of the insulin secretion stimulating action of BUF-3 measured by the static incubation method.

As shown in FIG. 7, secretion of insulin was observed as the concentration of BUF-3 increased.

The same results as BUF-3 may be obtained in the case of BUF-4 and BUF-5.

Obviously, numerous modifications and variations of the present invention are possible in light of the above teachings. It is therefore to be understood that within the scope of the appended claims, the invention may be practice otherwise then as specifically described herein.

What is claimed as new and desired to be secured by Letters Patent of the United States is:

1. A method of reducing the blood sugar level of an animal or human in need thereof, comprising administering to said animal or human a polypeptide selected from the group consisting of BUF-3, polypeptides containing at least 80% of the amino acid sequence of BUF-3 and mixtures thereof, in an amount sufficient to reduce the blood sugar level in said animal or human.

2. The method of claim 1, wherein said polypeptide is administered in an amount of 0.01–100 mg polypeptide per day.

3. The method of claim 1, wherein said polypeptide is administered parenterally.

4. The method of claim 1, wherein said polypeptide contains at least 90% of the amino acid sequence of BUF-3.

* * * * *

UNITED STATES PATENT AND TRADEMARK OFFICE
CERTIFICATE OF CORRECTION

PATENT NO. : 5,240,911   Page 1 of 2
DATED : August 31, 1993
INVENTOR(S) : Yasuo Totsuka, et al It is certified that error appears in the above-indentified patent and that said Letters Patent is hereby corrected as shown below:

Column 2, Line 7, "secreting folicle" should read --secreting follicle--

Column 2, Line 13, "secreting folicle" should read --secreting follicle--

Column 2, Line 22, "releasing folicle" should read --releasing follicle--

Column 4, Line 15, "(1)Psychochemical" should read --(3)Psychochemical--

Column 5, Line 17, "smaller does" should read --smaller doses--

Column 7, Table 1, "GPT IU/l)" should read --GPT (IU/l)--

Column 9, Line 12, "24mM of $NaHCO_3$" should read --24mM of $NaHCO_3$,--

Column 9, Line 26, "$2H_2$" should read --$2H_2O$--

UNITED STATES PATENT AND TRADEMARK OFFICE
CERTIFICATE OF CORRECTION

PATENT NO. : 5,240,911

DATED : August 31, 1993

INVENTOR(S) : Yasuo Totsuka, et al

It is certified that error appears in the above-indentified patent and that said Letters Patent is hereby corrected as shown below:

```
Column 10, Line 36, "may be practice" should read --may be
practiced--
```

Signed and Sealed this

Sixth Day of December, 1994

*Attest:*

BRUCE LEHMAN

*Attesting Officer*     *Commissioner of Patents and Trademarks*